United States Patent [19]

Chiovini et al.

[11] 4,390,698

[45] Jun. 28, 1983

[54] DETHEOBROMINATION OF COCOA

[75] Inventors: Jacky Chiovini, Daillens; Maurice Blanc, Morges; Geoffrey Margolis, Bussigny, all of Switzerland

[73] Assignee: Societe d'Assistance Technique pour Produits Nestle S.A., Lausanne, Switzerland

[21] Appl. No.: 266,091

[22] Filed: May 21, 1981

[51] Int. Cl.³ ............................................ C07D 473/10
[52] U.S. Cl. ...................................... 544/274; 426/431
[58] Field of Search ................. 544/274, 275; 426/431

[56] References Cited

U.S. PATENT DOCUMENTS 2,416,484   2/1947   Kremers ............................... 544/274
4,160,042   7/1979   Farr et al. ............................ 544/274

Primary Examiner—Paul M. Coughlan, Jr.
Attorney, Agent, or Firm—Vogt & O'Donnell

[57] ABSTRACT

A process for the recovery of theobromine from an aqueous solution containing theobromine extracted from cocoa material, which comprises contacting the solution with a substantially neutral adsorbent and separating the adsorbent, with theobromine adsorbed thereon, from the aqueous solution of reduced theobromine content.

10 Claims, No Drawings

DETHEOBROMINATION OF COCOA

The present invention is concerned with the recovery of theobromine from aqueous media.

The preparation of soluble cocoa by the extraction of cocoa material with water is well-known. During the extraction process theobromine is extracted along with other water-soluble solid materials. However, it is often desirable to prepare a soluble cocoa substantially free from stimulating substances such as theobromine and these may be removed from the extract by adsorption on a solid adsorbent after which the theobromine-free extract is returned to the cocoa material. Various solid adsorbents have been suggested such as polymeric resins and activated carbon but they can cause a deterioraton in the colour of the cocoa material. For example, if activated carbon is used, the contact between the aqueous extract and activated carbon often leads to an increase in pH which is associated with the deterioration in the colour of the cocoa material.

We have now found that this undesirable deterioration in colour may be considerably diminished if the adsorbent used shows a substantially neutral reaction on dispersion in water.

According to the present invention there is provided a process for the recovery of theobromine from an aqueous solution containing theobromine extracted from cocoa material, which comprises contacting the solution with a substantially neutral adsorbent and separating the adsorbent with theobromine adsorbed thereon, from the aqueous solution of reduced theobromine content. The term "substantially neutral" used to describe the adsorbent means that when the adsorbent is immersed in water the pH value is substantially unchanged. An example of a resin adsorbent having this property is semi-calcinated resin XE-340 manufactured by Rohm & Haas. However it is preferred to use activated carbon having this property which may be obtained either by acid washing of thermally activated carbon followed by rinsing with water to neutrality, or by neutralisation of acid-activated carbon with an aqueous alkali followed by rinsing with water to neutrality.

The aqueous solution containing theobromine may be extracted from cocoa material by conventional methods, involving contact of the cocoa material with an aqueous medium which may be water, preferably deionised water, an aqueous solution of non-theobromine cocoa solids, or an aqueous solution of non-theobromine cocoa solids containing a minor amount of theobromine, for a period of time sufficient to reduce the theobromine content of the cocoa material to the desired level. The cocoa material may be any cocoa-containing mass, for example green cocoa beans, roasted cocoa beans or roasted cocoa nibs, but is preferably the green, ground, unroasted cocoa nibs formed by cleaning, cracking and winnowing the cocoa beans to remove filth, germs and most of the shell material, followed by grinding. The extraction may be carried out batchwise or in a continuous counter-current extraction system containing a plurality of columns.

The ratio of water to the cocoa material during the extraction is not critical but is in general determined having regard to practical considerations imposed by industrial operations. Excessive volumes of water should be avoided, as also water to cocoa ratios which do not provide for adequate theobromine extraction. Conveniently, a weight ratio of water to cocoa material from 5 to 200 parts and preferably from 10 to 100 parts of water per part of cocoa material gives satisfactory results.

In a batchwise extraction process, a fixed weight of the cocoa material is contacted as a static bed, in a column, or in a suitable tumbler or like extractor with a fixed volume of water. The water is continuously recycled whereby theobromine-laden water is withdrawn from the column or extractor and detheobrominated by contacting a neutral adsorbent contained in another column, prior to its return to the cocoa material. The total contact time will depend, inter alia on the water/cocoa ratio, the temperature, and the degree of detheobromination desired and is usually from 1 to 10 hours, preferably from 2 to 3 hours. The temperature may be, for example, from 40° to 100° C., preferably from 70° to 95° C. at atmospheric pressure, or higher if the extraction takes place under pressure.

In a continuous counter-current extraction process, water passes through an extraction system comprising a plurality of cells containing the cocoa material whereby the water enters the extraction system at a cell containing the most exhausted batch of cocoa material, passes through progressively fresher batches of cocoa material contained in successive cells and is finally drawn off from the cell containing the freshest batch of cocoa material. The temperature of the water entering the cell containing the most exhausted cocoa material may be from 40° to 100° C. preferably from 70° to 95° C. at atmospheric pressure, or higher if the extraction takes place under pressure. The number of cells and cycle time are chosen to give the desired detheobromination. Up to eight cells, in series, may be used with a cycle time of from 15 to 120 minutes.

The aqueous extract containing theobromine and non-theobromine solids may be concentrated before being detheobrominated by contacting with the neutral adsorbent, for example in a counter-current system. In such a system the adsorbent is contained in several columns and the extract passes through these columns in series. Periodically the most saturated column is removed from the system and one containing fresh adsorbent added. The temperature in the columns is conveniently above 40° C. and preferably from 70° to 95° C. The number of columns, the cycle time for each column and the residence time of the extract are chosen to achieve the degree of detheobromination desired and to minimise the quantity of carbon used. The weight of adsorbent is usually from 10 to 20% of the weight of cocoa material being detheobrominated. If desired, the theobromine content of the aqueous solution may be reduced substantially to zero by the process.

During contact of the aqueous extract with the neutral adsorbent a proportion of the non-theobromine solids are adsorbed in addition to the theobromine. Part of these adsorbed solids, for example, 70 to 80%, can be recuperated without desorbing the theobromine by washing the adsorbent, for example with water.

Whether the adsorbent is used in the batch or the counter-current continuous system, provision is advantageously made for continuity of operation by duplicating the beds of adsorbent so that one or more may be renewed whilst the others are on stream.

After the detheobromination is terminated, it is usually desirable, to avoid excessive losses to reincorporate the non-theobromine solids present in the aqueous extract into the cocoa material having a reduced content of theobromine.

Various techniques may be used. For example, the cocoa material may be pre-dried, at a temperature below 100° C., preferably from 60° to 70° C., preferably to a moisture content of from 2 to 7.5% and combined directly with the extract. Alternatively, the extract may be pre-concentrated, for example, by evaporation, to a solids content of from 5% to 25% before contact with the cocoa material. Preferably both the cocoa material and the extract are treated in this way, that is, the cocoa material is pre-dried and the extract pre-concentrated before the reincorporation.

Satisfactory reincorporation of the solids may be obtained after 2 hours, preferably from 5 to 8 hours, at a temperature above 40° C. and preferably from 60° to 80° C. Desirably, the total amount of water present is such that the final moisture content of the cocoa material is from 30 to 60%, preferably from 50 to 55%.

The cocoa material containing the reincorporated solids is then dried to a moisture content of 2 to 5% by weight before being roasted. The roasted material may be used in the normal way for the production of cocoa drinks or chocolate.

In a modification, the amount of non-theobromine solids contacted with the cocoa material may be less than the amount extracted during detheobromination.

Periodically, the adsorbent may be regenerated, usually by heating or solvent extraction. If desired, the theobromine may be recovered from the adsorbent by solvent extraction, for example, with an aliphatic alcohol such as ethanol or a chlorinated hydrocarbon, such as methylene dichloride.

The following Examples further illustrate the present invention. Parts and percentages are expressed by weight unless otherwise stated.

EXAMPLE 1

Neutralised activated carbon was prepared by washing commercial thermally activated carbon with 2% hydrochloric acid followed by rinsing with deionised water (pH=6) until the pH of the washings is constant at 6.0.

100 parts of green, ground unroasted cocoa nibs were contacted at 80° C. in a column with 1,100 parts of water. Clear-brown theobromine-laden water was continuously withdrawn from the column and detheobrominated by contacting neutral activated carbon contained in another column and recycled to the cocoa nibs. After two hours the brown aqueous extract was concentrated by evaporation to 90 parts. The exhausted cocoa nibs were dried at 65° C. for 18 hours until the moisture content was reduced to 5%. The concentrated aqueous extract was reincorporated into the dried cocoa nibs in a mixer at 70° C. for 6 hours to give a cocoa material containing 53% moisture. The cocoa material having all the soluble materials reincorporated therein was dried at 70° C. for 12 hours and then roasted. The amount of theobromine was reduced from 1.30% to 0.04%. Whereas the colour of the detheobrominated extract showed only a slight difference from the theobromine-laden extract, the colour of an extract, which had been detheobrominated by contacting unwashed carbon, was greyish-black.

EXAMPLES 2 to 6

A similar procedure to that described in Example 1 was followed except that the time of contact, the temperature, the water: cocoa ratio, the loss of non-theobromine solid materials and the degree of detheobromination (DTB) achieved are given in the following Table.

TABLE I

| Example | Time of contact (hours) | Temp. (°C.) | Water:Cocoa ratio | Loss of solid materials % | DTB % |
|---|---|---|---|---|---|
| 2 | 2 | 60 | 10 | 9.4 | 64 |
| 3 | 2 | 80 | 10 | 11.0 | 76 |
| 4 | 2 | 95 | 10 | 11.0 | 82 |
| 5 | 2 | 95 | 20 | 11.6 | 92 |
| 6 | 3 | 80 | 100 | 17.4 | 98 |

EXAMPLE 7

A similar procedure to Example 3 was followed but in which the water was forced to flow from the bottom to the top of the column containing the cocoa nibs. The loss of solid materials was 10.5% while the amount of detheobromination was 90.4%.

EXAMPLE 8

Green, ground, unroasted cocoa nibs were formed by cleaning, cracking and winnowing the cocoa beans to remove filth, germs and most of the shell material, followed by grinding. These green, ground, unroasted cocoa nibs were detheobrominated continuously by counter-current extraction with an aqueous solution. 4 extractors in series were used, each containing 200 parts of the cocoa nibs. The extraction was carried out with deionised water at 80° C. entering the most exhausted extractor. A clear brown aqueous solution containing theobromine and non-theobromine solids was removed at 80° C. from the extractor containing the least exhausted cocoa, the cycle time being 30 minutes. The last extractor containing detheobrominated cocoa was removed from the system and one containing fresh green, ground, unroasted cocoa nibs was added once every two hours. The ratio of water to cocoa nibs was 10:1 so that the flow rate of water through the system was 2,000 parts/hr and the aqueous solution removed contained 1% dissolved solids.

The extract coming from the least exhausted cocoa was passed countercurrently through 2 columns in series, each column containing 50 parts of neutralised, activated carbon prepared in a manner similar to that described in Example 1. The temperature in the columns was maintained at 80° C. The most saturated carbon column was removed and a fresh one added every 4 hours. The saturated carbon columns were washed with water flowing at 2,000 parts/hr and the brown aqueous solution removed contained 0.7% dissolved non-theobromine solids.

The detheobrominated cocoa nibs were dried to a moisture content of 5% and mixed with the corresponding detheobrominated extract containing dissolved non-theobromine solids, which has first been concentrated by evaporation to contain 7% solids. Thereafter, the cocoa nibs containing 50% moisture were dried to 5% moisture content. The degree of detheobromination was 97%.

EXAMPLE 9

A similar procedure to that described in Example 1 was followed except that the clear brown theobromine-laden water was detheobrominated by contacting it with semi-calcinated resin XE-340 manufactured by Rohm & Haas. The colour of the detheobrominated extract was also clear brown showing no difference from the theobromine-laden water.

We claim:

1. A process for recovering theobromine from an aqueous solution containing theobromine extracted from cocoa material comprising:
   (a) contacting the solution with a substantially neutral adsorbent; said adsorbent having the characteristic that when immersed in water, the pH of the water remains essentially unchanged; and then
   (b) separating the adsorbent laden with theobromine from the aqueous solution of reduced theobromine content.

2. The process of claim 1, wherein the cocoa material is the green, ground, unroasted cocoa nibs formed by cleaning, cracking and winnowing the cocoa beans to remove filth, germs and most of the shell material, followed by grinding.

3. The process of claim 1, wherein the contacting is effected at a temperature of from 70° to 95° C.

4. The process of claim 1, wherein the theobromine content of the aqueous solution is reduced substantially to zero and the non-theobromine solids therein are combined with the cocoa material having a reduced content of theobromine and other water-soluble solid materials.

5. A process for the removal of theobromine from cocoa material characterised in that the cocoa material is contacted with an aqueous medium; the aqueous medium containing theobromine dissolved from the cocoa material is recovered; theobromine is removed from this medium by contact with a substantially neutral activated carbon, which carbon has the characteristic that when immersed in water, the pH of the water remains essentially unchanged; the carbon with theobromine adsorbed thereon is separated from the aqueus medium of reduced theobromine content; and the non-theobromine solids present in the aqueous medium of reduced theobromine content is combined with cocoa material having a reduced content of theobromine and of non-theobromine solids.

6. The process of claim 1, wherein the theobromine content of the aqueous medium is reduced substantially to zero.

7. The process of claim 1, wherein the adsorbent is substantially neutral activated carbon.

8. A process for recovering theobromine from an aqueous solution containing theobromine extracted from cocoa material comprising:
   (a) contacting the solution with a substantially neutral activated carbon; said carbon having the characteristic that when immersed in water, the pH of the water remains essentially unchanged; and then
   (b) separating the activated carbon laden with theobromine from the aqueous solution of reduced theobromine content.

9. The process of claim 8, wherein the substantially neutral activated carbon is prepared by acid washing thermally activated carbon and then rinsing the acid treated activated carbon with water to neutrality.

10. The process of claim 8, wherein the substantially neutral activated carbon is prepared by neutralizing acid-activated carbon with aqueous alkali and then rinsing the alkali treated activated carbon with water to neutrality.

* * * * *

UNITED STATES PATENT AND TRADEMARK OFFICE
CERTIFICATE OF CORRECTION

PATENT NO. : 4,390,698
DATED : June 28, 1983
INVENTOR(S) : Jacky Chiovini, Maurice Blanc and Geoffrey Margolis It is certified that error appears in the above—identified patent and that said Letters Patent is hereby corrected as shown below:

Column 6, line 13 (line 1 of Claim 6), "1" should read --5--.

Signed and Sealed this

Fourth Day of October 1983

[SEAL]

Attest:

GERALD J. MOSSINGHOFF

Attesting Officer

Commissioner of Patents and Trademarks